United States Patent [19]

Bareth et al.

[11] 4,033,040
[45] July 5, 1977

[54] CLAMPING DEVICE FOR DENTAL TOOLS

[75] Inventors: Erich Bareth, Ummendorf; Hans Loge, Biberbach, both of Germany

[73] Assignee: Kaltenbach & Voigt, Biberach an der Riss, Germany

[22] Filed: Jan. 16, 1976

[21] Appl. No.: 649,806

[30] Foreign Application Priority Data

Dec. 10, 1975 Germany .......................... 2555617

[52] U.S. Cl. ................................. 32/27; 81/52.4 R
[51] Int. Cl.[2] .................... A61C 1/10; B25D 23/142
[58] Field of Search ............. 32/27, 26; 81/52.4 R, 81/52.4 A, 55; 64/29

[56] References Cited
UNITED STATES PATENTS 3,960,039   6/1976   Nash ...................................... 32/27

*Primary Examiner*—Robert Peshock

[57] ABSTRACT

A device for clamping and unclamping dental tools as, for example, drills, in a dental handpiece with an angled head in which the tool is held by means of a two-part clamping unit. One part of this clamping unit has a collet for holding the tool, and the other part of the clamping unit has a driven rotary hollow shaft located in the head. The collet is movable lengthwise inside the hollow shaft. To assume its clamped or unclamped position, the collet and hollow shaft are threadable into one another. One of the two parts of the clamping unit has at least one key surface accessible from the exterior at the tool end of the head. The other part of the clamping unit has also at least one key surface accessible from the exterior. A U-shaped carrier is provided with a first flange having a stationary key with parts for engagement with the key surfaces located at the tool end of the head. The other flange of the carrier has a pin-shaped key projecting into the area between the two flanges and axially movable in a hollow space of an exterior attachment of this other flange against the action of a spring in the direction away from the first flange. The pin-shaped key can be rotated manually by means of a knob on the key and projecting from the attachment. The pin-shaped key has a handle mounted on the U-shaped carrier and is actuatable by finger pressure applied transversely to the longitudinal axis of the key to axially move the key against the action of the spring.

9 Claims, 6 Drawing Figures

CLAMPING DEVICE FOR DENTAL TOOLS

BACKGROUND OF THE INVENTION

The present invention relates to a device for clamping and unclamping dental tools, e.g., drills, in a dental handpiece with an angled head in which the tool is held by means of a two-part clamping device. One part of this clamping device is in the form of a collet which holds the tool, and the other part is in the form of a driven rotary hollow shaft located in the head. Inside the hollow shaft, the collet can be moved lengthwise. In order to assume its clamped or unclamped position, collet and collet shaft can be threaded into one another by means of an outside thread on the collet and an inside thread in the hollow shaft. One of the two parts of the two-part clamping device is provided at the tool end of the head with at least one key surface accessible from the outside. The other part of the two-part clamping device on the end opposite to the tool end of the head also has at least one key surface accessible from the outside.

The device for clamping and unclamping comprises an essentially U-shaped carrier whose one flange has a stationary key with engaging means for engagement with the key surfaces located at the tool end of the head. The other flange has a pin-like key which projects into the area between the two flanges and is axially movable in an axial hollow space of an outside attachment of the flange against the action of a spring in the direction away from the first flange. This pin-like key can be rotated manually by means of a knob on the key end projecting from the attachment and, at the end opposite the knob, has engaging means for engaging the key surfaces located at the end opposite the tool end of the head.

In such devices, due to the movement of the pin-like key against the action of the spring, i.e., in the direction away from the opposite flange, the end of this key which is provided with engaging means is moved in the direction of the outside attachment of the flange receiving the pin-like key so that there is enough room for introducing the head of the dental handpiece into the region between the two flanges. At the same time, the user aligns and engages the key surfaces provided at both ends of the dental handpiece with the engaging means of both the stationary and the pin-like key. The pin-like key, under the action of the spring, is moved back to the aforementioned engagement position.

By holding the handpiece with one hand and turning the head of the pin-like key with the other hand, with the head or the part of the dental handpiece adjoining the head contacting the stringer of the U-shaped carrier, that part of the two-piece clamping device of the head of the dental handpiece whose key surfaces engage the engaging means of the pin-like key, can now be twisted so that the aforementioned part is threaded into the other part of the clamping device. The collet performs a lengthwise motion in relation to the hollow shaft so that the collet, depending on the rotation of the head of the pin-like key, opens to release a clamped tool or closes for clamping a loosely inserted tool.

A device of this type is known from the brochure "STARFLITE futura" issued by Star Dental Mfg. Co., Inc. With this known device, the knob of this key, which is heavier then the remaining pin-like key, is both the actuating member for turning the key and the actuating member for the motion of the key against the action of the spring. The latter motion must be accomplished by pulling the knob against the action of the spring, which is cumbersome and difficult, since only one hand is available while the other hand holds the handpiece. In addition, the same hand must also turn the knob in the pulled state which still under the tension of the spring, thereby increasing the complexity of handling.

Only a relatively weak spring can be used, since otherwise the finger force of the hand holding the U-shaped carrier of the device would be too small for pulling the knob and the pin-like key in the axial direction against the action of the spring. However, a weak spring impairs the exact centering of the engaging means of the two keys with the key surfaces of the head in the dental handpiece.

It is, therefore, an object of the present invention to provide a device of the initially described type which makes possible convenient operation with only one hand at substantially small costs.

Another object of the present invention is to provide a device of the foregoing character, which is substantially reliable in operation and has a long operating life.

A further object of the present invention is to provide a dental device, as described, which may be economically maintained in service.

SUMMARY OF THE INVENTION

The objects of the present invention are achieved by providing that the axially movable pin-like key has a handle which is mounted on the U-shaped carrier and is actuated by finger pressure, applied transversely to the longitudinal axis of this key in order to axially move the key against the action of the spring.

The user, in order to effect axial movement of the pin-like key against the action of the spring, need not exert a tensile force of this key or its knob. Instead, he can conveniently hold the U-shaped carrier in one hand between the thumb and one finger of this hand, and at the same time move the thumb or the finger to the handle and pressing it slightly. Enough finger force is available for this pressing action, so that a relatively strong spring may be used which upon release of the handle facilitates centering (alignment) of the engaging means of the two keys of the U-shaped carrier with the key surfaces of the angled head of the dental handpiece.

Exact alignment and handling of the device is further simplified if the stationary key has a cup facing the axially movable pin-like key to accommodate that part of the clamping device provided with key surfaces at the tool end of the head; the cup has a perforation for inserting the dental tool.

Also, to improve the alignment and tight grip of the key surfaces, there is engaged with the engaging means of the stationary key, one part of the clamping device, and a fixed rotation of the pin-like key is facilitated as follows: The engaging means of the stationary key are formed by stringers which face the axially movable key and are located radially in relation to the center of the perforation for axial insertion of the dental tool. These stringers engage key surfaces formed by sidewalls of associated radial slits on the tool end of the head of the dental handpiece. This assures a perfect fit of the engaging means between said key surfaces.

If, in accordance with the aforementioned known device, the pin-like axially movable key is provided in the area of the end which faces the stationary key and which has the engaging means with a radial projection serving as a thrust bearing for the spring, while the other thrust bearing for the spring is formed by a radial projection of the attachment which forms a stop for limiting the movement of the pin-like key under the action of the spring; the following applies: The radial projection which forms the stop projects into the hollow space of the attachment and the strengthened shaft section, adjacent to the knob of the pin-like key abuts against this radial projection.

The handle, which is associated with the axially movable pin-like key, is formed by one arm of a two-arm actuation lever which is pivoted about an axis that runs transversely to the longitudinal axis of this key and which is located at the side of the hollow space in the attachment. The other arm of this actuating lever runs transversely to the longitudinal axis of the key. This arm is fork-shaped and encloses (reaches under) the strengthened shaft section of the key above the radial projection of the attachment. The actuating lever arm which constitutes the handle is bent downward from the fork-shaped arm.

The design of the special two-armed actuating lever with the above embodiment assures a particularly convenient handling of the U-shaped carrier. The two-armed feature of the actuating lever further facilitates the use of a stronger spring with its aforementioned advantages.

A very convenient support for the finger actuating the handle on the U-shaped carrier is provided if a trough is located on the attachment exterior and opposite the pivot axis.

An additional improvement results from the manufacture of the stringer or a stringer jacket for the U-shaped carrier from synthetic or similar material. The softness of the synthetic material prevents scratching or damage to the material of the dental handpiece when turning the knob of the pin-like key the head or that part of the dental handpiece adjoining the head comes in contact with the stringer of the U-shaped carrier, during the handling of the device. The aforementioned jacket may be made of a shrunk cover of synthetic or similar soft material.

Secure guidance when inserting the head of the dental handpiece into the area between the two flanges of the U-shaped carrier is facilitated if the stringer of the U-shaped carrier has a recess adapted to the shape of the angled head of the dental handpiece.

If the device for clamping and unclamping is used for several dental handpieces whose angled heads have different designs or dimensions or diameters, it is expedient for the adaptation to these different designs if the stringer of the U-shaped carrier comprises a shaft of circular cross section, and a sleeve rotatable about this shaft. On its exterior, the sleeve is provided with several recesses adapted to the shapes of the angled heads of the various dental handpieces.

In an advantageous further development of the last-mentioned embodiment, on at least one front end of the sleeve, there is provided locking means associated with the recesses. These locking means engage in spring fashion with the mating locking means located on the flange, of the U-shaped carrier, which faces this front end. This facilitates locking in the detent selected by suitable adjustment of the rotary sleeve. As a result, when turning the knob of the pin-like key, the head or that part of the dental handpiece adjoining the head comes in contact with the stringer of the U-shaped carrier, without running the risk of an unintentional turning of the sleeve and hence improper contact with the head.

The novel features which are considered as characteristic for the invention are set forth in particular in the following description. The invention, both as to its construction and its method of operation, together with additional objects and advantages thereof, will be best understood from the description of specific, exemplary embodiments when read in connection with the accompanying drawings.

DESCRIPTION OF THE PREFERRED EMBODIMENTS

Figure 1:
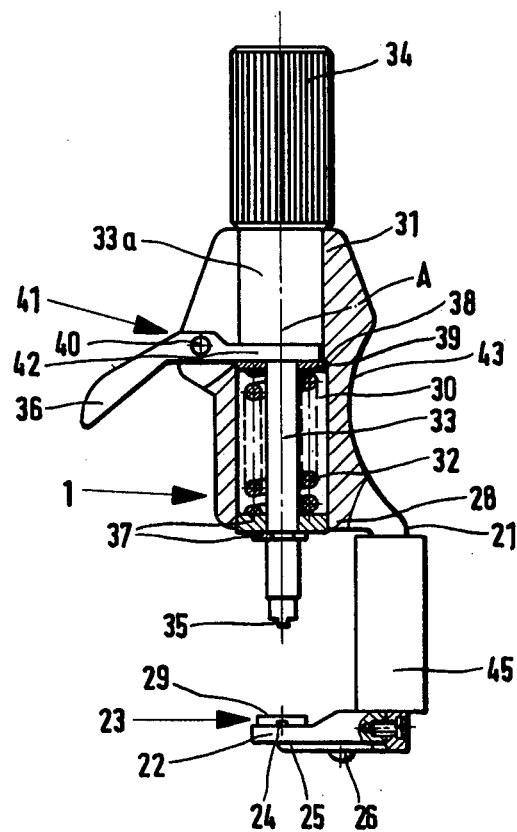
FIG. 1 is a partial section and a partial side view of the inventive device for clamping and unclamping.

The invention device 1 is used for clamping and unclamping of a dental tool (not shown), e.g., of a drill, in a dental handpiece 2 with an angled head 3 in which the tool is held by means of a two-part clamping device 4. According to FIG. 2, one part of the clamping device 4 comprises a collet 5 which holds the tool, while the other part comprises a rotary but axially-fixed hollow shaft 7 which is driven by means of bearings 6 in head 3.

In order to facilitate the rotary drive, the hollow shaft 7 is a rotor with turbine vanes 8 which may be driven by a pressure agent, e.g., compressed air, in order to achieve rotation of the hollow shaft 7 in a manner that is of no interest here and therefore is not shown. The hollow shaft holds a tubular insert 7a which is rigidly affixed to the hollow shaft. For this reason parts 7 and 7a can virtually be considered as one piece.

The collet 5 can be moved lengthwise inside hollow shaft 7. In order to obtain the clamped position or the unclamped position of collet 5, the collet and hollow shaft can be threaded into one another by means of an outside thread 9 located on the interior end of collet 5 and an inside thread 10 located in the hollow shaft 7.

Figure 2:
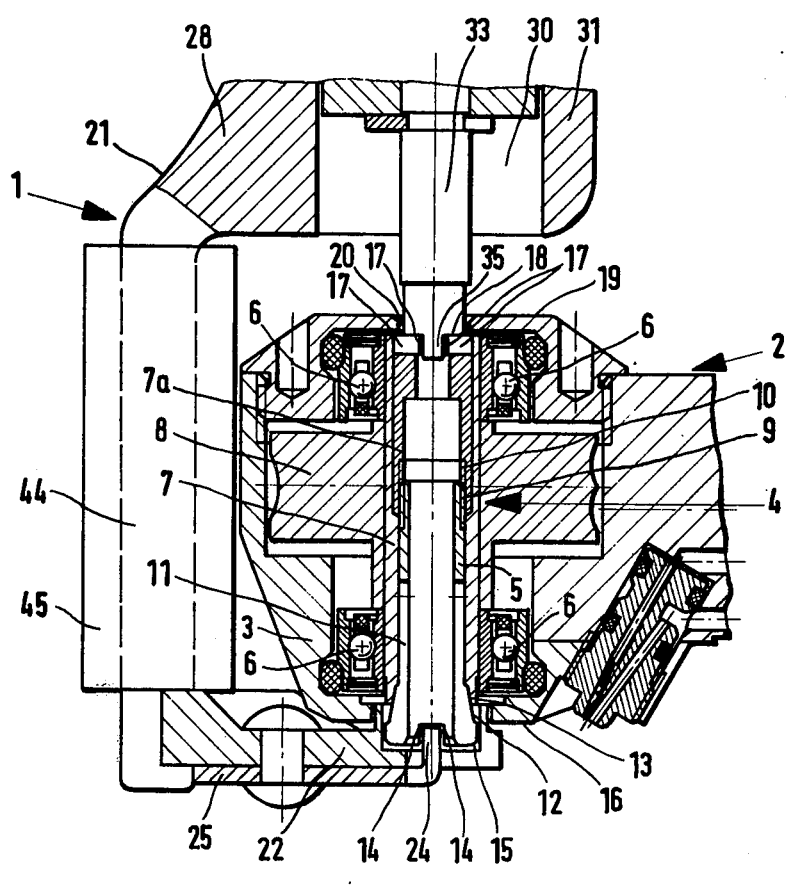
FIG. 2 is a sectional view and shows the device of FIG. 1 on an enlarged scale, mated with an angled head of a dental hand tool.

The collet 5 has, at its tool end, shown at the bottom in FIG. 2, resilient clamping tongues separated from one another by slits 11. In the lower region of slits 11, the collet 5 has an outer conical expanse 12, while the hollow shaft 7 at the same end as the collet 5 has an interior conical expanse 13 corresponding to expanse 12. If collet and hollow shaft are revolved in opposite directions in such a way that the collet 5 is unscrewed from the hollow shaft 7, the tongues of collet 5 open so that the latter assumes its unclamped position. Alternatively, if collet 5 is screwed in the opposite direction into hollow shaft 7, the clamping tongues of collet 5 close so that the latter assumes its clamped position.

In the case of FIG. 2, one of the two parts of clamping device 4, collet 5, is provided in the area of the tool end of head 3, i.e., at the conically tapered end, with key surfaces 14 accessible from without. These surfaces are formed by the side walls of the slits located in the front surface 15 of collet 5. In order to facilitate the aforementioned accessibility of key surfaces 14, collet 5 projects with its front surface 15 from the tool-side front wall 16 of head 3 so that the key surfaces 14 are exposed.

In a similar manner, in the case of FIG. 2, the other part of the clamping device 4, hollow shaft 7, has at its end facing the tool-side end of head 3, key surfaces 17. These are accessible from the outside, and they are formed by the side walls of two intersecting slits located in the front wall 18 of hollow shaft 7. In order to facilitate the aforementioned accessibility of the key surfaces 16, the front wall 19 of head 3 faces the tool-side front wall 16 and has an opening 10 which exposes the greater part of key surfaces 17.

Figure 5:
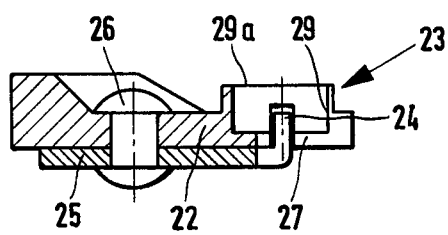
FIG. 5 shows a section of a lower flange in FIG. 1 of a U-shaped carrier constituting the device.
Figure 6:
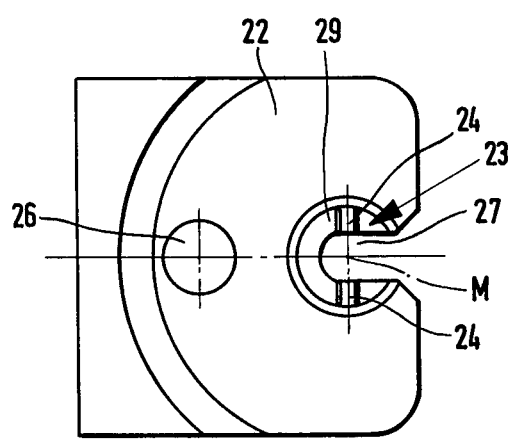
FIG. 6 is a top view of the flange of FIG. 5.

The device 1 for clamping and unclamping comprises an essentially U-shaped carrier 21 with one flange 22 having a stationary key 23 with engaging means 24 for engagement with the key surfaces 14. In accordance with FIGS. 5 and 6, the engaging means 24 are formed by two spaced rectangular bends of a strip 25 which is fastened by means of a rivet 26 or similar fastener to the underside of flange 22. The flange 22 or the key 23, between the two bends constituting the engaging means 24, has a perforation 27 that facilitates the lateral introduction and the axial insertion of the dental tool. The bends constituting the engaging means 24 are thus stringers located radially in relation to the center M of perforation 27. These stringers face the second flange 28 of the U-shaped carrier 21.

Furthermore, the stationary key 23 has a cup 29, formed by a round wall, which, with its opening 29a, faces the second flange 28 and serves to accommodate and center that end of collet 5 which has key surfaces 14.

The flange 28 of U-shaped carrier 21 has a pin-like key 33 which projects into the area between the two flanges 22, 28, and is axially movable in an axial hollow space 30 of an outside attachment 31 of flange 28 against the action of a spring 32 in the direction away from the first flange 22. This pin-like key 33 can be rotated manually by means of a knob 34 on the key end projecting from attachment 31 and, at the end facing knob 34, has engaging means 35 for engaging key surfaces 17. Thus, engaging means 35 has the shape of the free end of a screwdriver.

The axially movable pin-shaped key 33 has a handle 36 which is mounted on the U-shaped carrier 21 and is actuated by finger pressure, applied transversely to the longitudinal axis A of this key 33 in order to axially move key 33 against the action of spring 32.

As shown in FIG. 1, the pin-shaped axially movable key 33, in the region of its end which faces the stationary key 23 and contains the engaging means 35, is provided with a radial projection 37 that serves as a thrust bearing for spring 32; the other thrust bearing for spring 32 is formed by a radial projection 38 of attachment 31 that forms a stop for limiting the movement of pin-shaped key 33 under the action of spring 32. Between radial projection 38 of attachment 31 and spring 32, which is a compression spring, there is an intermediate disk 39 with an insertion opening for pin-shaped key 33.

The radial projection 38 constituting the stop projects into the hollow space 30 of attachment 31. A reinforced shaft section 33a of this key, adjacent to knob 34 of pin-like key 33, abuts against this radial projection 38 or against intermediate disk 39. The handle 36, which is assigned to the axially movable pin-like key 33, is formed by one arm of a two-arm actuation lever 41 which is pivoted about an axis 40. The latter runs transversely to the longitudinal axis A of this key, located at the side of hollow space 30 in attachment 31. The other arm 42 of actuating lever 41 runs transversely to the longitudinal axis A of pin-like key 33. The arm 42, furthermore, is fork-shaped and encloses the reinforced shaft section 33a of pin-like key 33 above radial projection 38 of attachment 31 and above intermediate disk 39. The arm of actuating lever 41 which constitutes handle 36 is bent downward from the fork-shaped arm 42 at an angle of about 45°, as shown in FIG. 1.

On the exterior, of attachment 31, which faces pivot axis 40, a trough 43 is provided to accommodate the fingers of the operator.

A stringer 44 of U-shaped carrier 21 may be made of synthetic or similar material. Stringer 44 may also have a jacket 45 made of synthetic or similar soft material.

Figure 3:
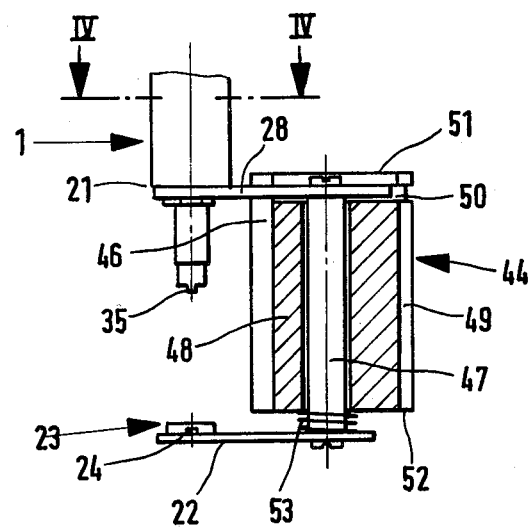
FIG. 3 is a sectional view and shows a modified embodiment of the lower part of the device shown in FIG. 1.
Figure 4:
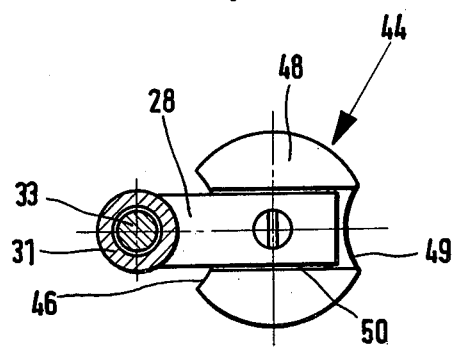
FIG. 4 shows a section taken along line IV—IV in FIG. 3.

Furthermore, the stringer 44 of U-shaped carrier 21 has a recess 46 which is adapted to the shape of the angled head 3 of the dental handpiece 2 and which runs in a longitudinal direction of stringer 44, as shown in FIGS. 3 and 4.

As indicated by FIGS. 3 and 4, stringer 44 of U-shaped carrier 21 comprises a shaft 47 of circular cross-section, and a sleeve 48 rotatable about this shaft 47. On its exterior, the sleeve 48 is provided with several recesses 46, 49 adapted to the shapes of the angled heads 3 of various dental handpieces.

On the front end of sleeve 48, shown in the upper part of FIG. 3, there are locking means 50, associated with the recesses 46, 49, which engages the mating engaging means of the flange 28 of the U-shaped carrier 21, that is adjacent to this front end. The locking means 50 is formed by a groove located in the front surface 51 of sleeve 48, while flange 28 itself represents the mating locking means. For a spring-like mating, a compression spring 53 is located between flange 22 and the front surface 52 of sleeve 48, facing front surface 51.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the spirit and scope of this invention.

We claim:

1. A device for clamping and unclamping dental tools in a dental handpiece with an angled head, comprising, in combination: two-part clamping means for holding a dental tool; one part of said clamping means having a collet for holding the dental tool and another part having a driven rotary hollow shaft located in the head, said collet being movable lengthwise inside said shaft, said collet and said shaft being threadable into one another by means of an outside thread on said collet and an inside thread in said shaft selectively to obtain clamped and unclamped positions, one of said parts of the clamping means having at the tool end of the head at least one key surface accessible from the exterior;

the other part of said clamping means having on the end opposite to the tool end also a least one key surface accessible from the exterior; a U-shaped carrier having a first flange with a stationary key, the latter having engaging means for engagement with said key surface at the tool end; a second flange of said carrier having an axially movable pin-shaped key projecting into the area between said flanges; an exterior attachment of said second flange with an axial hollow space, said movable key being axially movable in said hollow space against the action of spring means in a direction away from said first flange; a knob on the key end projecting from said attachment for manually rotating said movable key; and engaging means on said movable key at the opposite end of said knob for engaging said key surfaces at said opposite ends of the tool and of said head; said movable key having a handle mounted on said carrier and actuatable with hand of the operator by finger pressure applied transversely to the longitudinal axis of said movable key to axially move the latter by the same hand of the operator against the action of said spring means; wherein said handle constitutes a first arm of a two-arm acutation lever pivoted in a portion of said carrier and jutting out therefrom for easy actuation by the same hand of the operator, a second arm of said lever being fork-shaped and extending substantially transversely to the longitudinal axis.

2. A device for clamping and unclamping dental tools in a dental handpiece with an angled head, comprising, in combination: two-part clamping means for holding a dental tool; one part of said clamping means having a collet for holding the dental tool and another part having a driven rotary hollow shaft located in the head, said collet being movable lengthwise inside said shaft; said collet and said shaft being threadable into one another by means of an outside thread on said collet and an inside thread in said shaft selectively to obtain clamped and unclamped positions; one of said parts of the clamping means having at the tool end of the head at least one key surface accessible from the exterior; the other part of said clamping means having on the end opposite to the tool end also at least one key surface accessible from the exterior; a U-shaped carrier having a first flange with a stationary key, the latter having engaging means for engagement with said key surface at the tool end; a second flange of said carrier having an axially movably pin-shaped key projecting into the area between said two flanges; an exterior attachment of said second flange with an axial hollow space, said movable key being axially movable in said axial hollow space against the action of spring means in a direction away from said first flange; a knob on the key end projecting from said attachment for manually rotating said movable key; and engaging means on said movable key at the opposite end of said knob for engaging said key surfaces at said opposite ends of the tool and of said head; said movable key having a handle mounted on said carrier and manually actuatable by pressure applied transversely to the longitudinal axis of said movable key to axially move the latter against the action of said spring means; wherein said movable key has a radial projection forming a thrust bearing for said spring means in the region of the end of said movable key that faces said stationary key; another thrust bearing for said spring means being formed by a radial projection of said attachment, the latter forming a stop for limiting the movement of said movable key under the action of said spring means; said radial projections projecting into said axial hollow space; a reinforced shaft section adjacent to said knob of said movable key abutting against said radial projections; and a two-arm actuation lever pivoted about an axis and forming said handle by one of its arms, the axis of said lever extending transversely to the longitudinal axis of said movable key, the other arm of said lever extending transversely to the longitudinal axis; said other arm being fork-shaped and extending under said shaft section above said radial projections; and said one arm being bent downward from said other arm.

3. The device as defined in claim 2, wherein said stationary key has a cup with an opening facing said movable key, said cup lodging a part of said clamping means at the tool end of the head and having key surfaces; said cup having a perforation for insertion of the dental tool.

4. The device as defined in claim 3, wherein said engaging means includes stringer means facing said movable key and being radially located with respect to the center of said perforation, said stringer means engaging said key surfaces that are formed at the tool end of the head through side walls of associated radial slits.

5. The device as defined in claim 2, further comprising trough means on the outside of said attachment, facing the pivot axis of said lever to serve as a support for fingers of the operator.

6. The device as defined in claim 2, wherein said carrier has stringer means of synthetic material.

7. The device as defined in claim 6, wherein said stringer means has a recess conforming to the shape of the angled head.

8. The device as defined in claim 6, wherein said stringer means includes a shaft of circular cross-section; and further comprising a sleeve rotatable about said shaft; said sleeve having a plurality of recesses on the exterior thereof and conforming to shapes of angled heads of different dental handpieces.

9. The device as defined in claim 8 further comprising locking means on at least one front end of said sleeve; first mating locking means on said second flange of the carrier that faces said front end of the sleeve and is in spring-tight engagement with said first locking means, which latter is associated with said recesses on the exterior of said sleeve.

* * * * *